United States Patent [19]
Wedel et al.

[11] Patent Number: 5,088,500
[45] Date of Patent: Feb. 18, 1992

[54] ULTRASOUND FINGER PROBE AND METHOD FOR USE

[75] Inventors: Victor J. Wedel, Rt. 3, Box 121, Washington, Iowa, 52353; Rick L. Pruter, Davenport, Iowa

[73] Assignee: Victor J. Wedel, Washington, Iowa

[21] Appl. No.: 440,881

[22] Filed: Nov. 22, 1989

[51] Int. Cl.⁵ ............................................. A61B 8/12
[52] U.S. Cl. ............................................. 128/662.06
[58] Field of Search ..................... 128/660.01, 662.06

[56] References Cited

U.S. PATENT DOCUMENTS

| | | | |
|---|---|---|---|
| 4,469,106 | 9/1984 | Harui | 128/662.05 |
| 4,542,747 | 9/1985 | Zurinski et al. | 128/660 |
| 4,545,386 | 10/1985 | Hetz et al. | 128/662.06 |
| 4,635,644 | 1/1987 | Yagata | 128/660 |
| 4,742,829 | 5/1988 | Law et al. | 128/662.06 X |
| 4,883,059 | 11/1989 | Stedman et al. | 128/660.01 |
| 4,898,178 | 2/1990 | Wedel | 128/662.05 |
| 4,911,173 | 3/1990 | Terwilliges | 128/662.06 |
| 4,972,839 | 11/1990 | Avgelson | 128/662.06 |

FOREIGN PATENT DOCUMENTS 3807004 9/1988 Fed. Rep. of Germany ............ 128/662.03

*Primary Examiner*—Francis Jaworski
*Attorney, Agent, or Firm*—Gregory G. Williams

[57] ABSTRACT

A method and apparatus for performing ultrasound rectal examinations, by providing an ultrasound transducer which is slipped over the physician's finger tip and then inserted into the patient's rectum, together with an apparatus for guiding medical instruments into the area to be imaged.

15 Claims, 1 Drawing Sheet

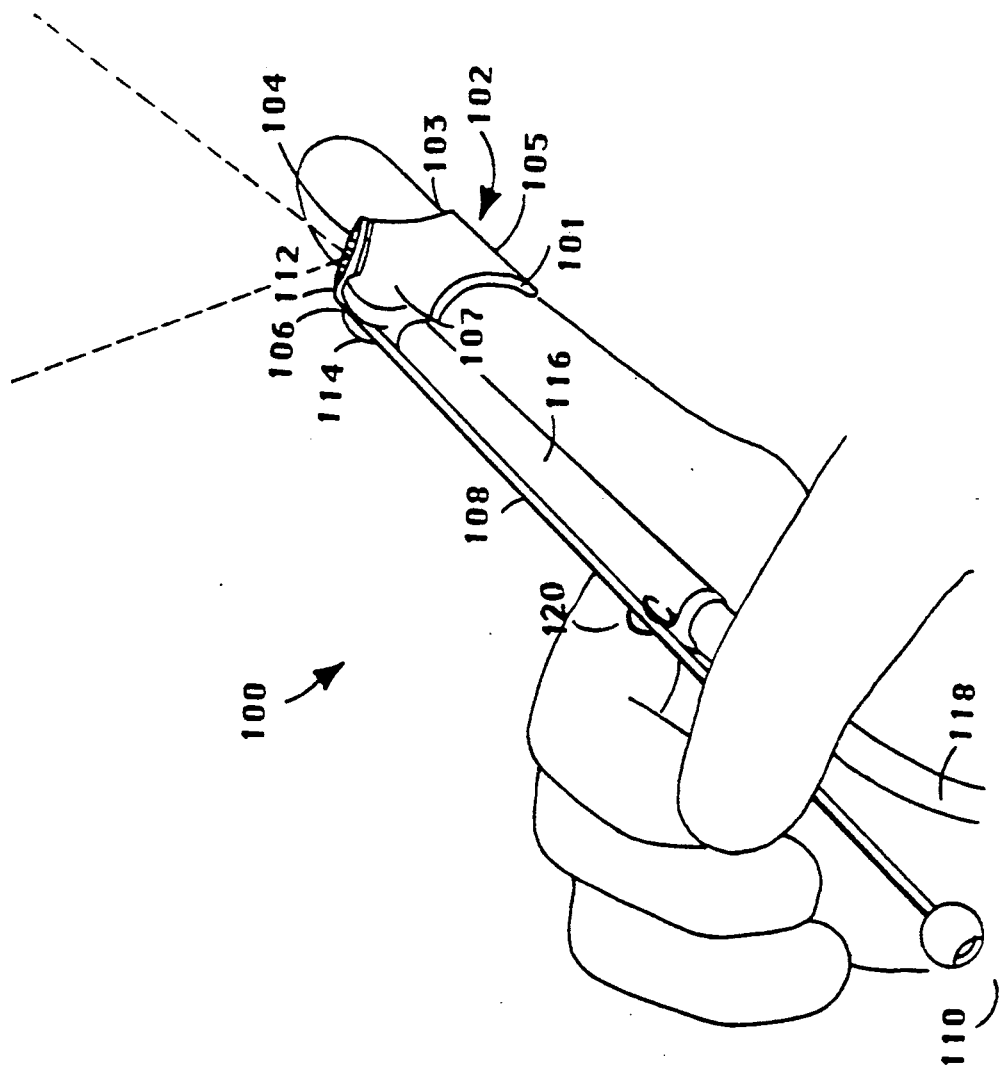

ULTRASOUND FINGER PROBE AND METHOD FOR USE

CROSS-REFERENCE TO RELATED APPLICATION

This application generally relates to a copending U.S. patent application entitled "Needle Guide for Ultrasound Transducers" filed on Nov. 8, 1989, by Victor J. Wedel and Rick J. Pruter, which is incorporated herein by this reference in its entirety.

FIELD OF THE INVENTION

The present invention relates to ultrasound transducers and ultrasound imaging systems and more particularly relates to an ultrasound transducer probe for attachment to a human finger and even more particularly concerns such a finger probe having a medical instrument guide therein.

BACKGROUND OF THE INVENTION

In the past, ultrasound transducers and ultrasound imaging systems have enjoyed much use throughout the medical profession. One particular use in which ultrasound transducers have gained wide spread acceptance is in rectal imaging associated with prostate examinations. Often these prostate examinations would involve a two step procedure; the first step being the insertion of the physician's finger into the patient's rectum, where a manual manipulation and palpation of the prostate gland is performed; and the second step being the insertion of a tube-like ultrasound transducer into the rectum for facilitating the ultrasound imaging of the prostate gland.

While this two-step procedure has been extensively performed in the past, it does have some serious drawbacks. Typically, the physician's finger is removed prior to the insertion of the tube-like transducer, in order to minimize discomfort for the patient. As a result, no imaging is possible during the manual palpation of the prostate. Furthermore, the positioning of the tube-like transducer is controlled from a point outside the body, and more distant from the desired imaging area.

Consequently, there exists a need for improvement in ultrasound imaging techniques and probes for use in prostate examinations where the imaging is possible at precisely controllable positions and during manual manipulation of the prostate gland.

SUMMARY OF THE INVENTION

It is an object of the present invention to allow for precise control of an ultrasound transducer during prostate examinations.

It is a feature of the present invention to provide and ultrasound transducer which is attached to the physician's finger during prostate examinations.

It is an advantage of the present invention to allow the physician to sense by touch the precise location of the prostate gland while concomitantly providing for precise positioning of the transducer.

It is a further object of the present invention to provide ultrasound imaging during manual manipulation of the prostate gland.

It is a further feature of the present invention to attach the ultrasound transducer at a distal position on the physician's finger where it is possible to provide ultrasound imaging, through the transducer, and concurrently allow the physician to perform palpations of the prostate.

It is a further advantage of the present invention to provide the physician with more visual information during the actual manual examination.

It is yet a further object of the present invention to increase the different possible directions of imaging of the prostate gland.

It is yet a further feature to have an adjustable transducer probe for providing different angles of imaging.

It is yet a further advantage to allow for both transverse and longitudinal imaging views of the prostate gland.

The present invention is designed to satisfy the aforementioned needs, fulfill the previously propounded objects including the above described features and achieve the earlier articulated advantages. The present invention is carried out in a "tube-like transducer-less" fashion in the sense that the tube-like transducer probes have been eliminated. Instead, a transducer is attached directly to the physician's finger and inserted into the patient's rectum.

Accordingly, the present invention includes an ultrasound imaging transducer probe which is attachable to the physician's finger prior to the manual rectal examinations.

BRIEF DESCRIPTION OF THE DRAWING

The present invention may be more fully understood by a reading of the detailed description in conjunction with the appended drawing, in which:

The FIGURE is a perspective view of the ultrasound finger probe of the present invention attached to a human finger.

DETAILED DESCRIPTION

While the discussion herein is being limited to the use of the probe of the present invention in rectal examinations of the prostate gland, it is understood that it is merely one of many possible uses of the present invention. The probe of the present invention is equally adaptable for use an a vaginal probe or for use in any other body cavity.

Now referring to the FIGURE, there is shown an ultrasound finger probe of the present invention generally designated 100. The probe 100 is shown disposed on a human finger.

Probe 100 is shown having a probe ring 102 having a bottom side 105, a top side 107, a palm end opening 101 and a tip end opening 103 therein and further with a transducer head 104 thereon. Preferably, the ring 102 is constructed of an impact resistant yet resilient material such as plastic. The head 104 is of similar basic functional design as others well known in the art and essential is a means for generating an ultrasound signal in response to an input electrical signal and also a means for receiving reflected ultrasound signals and generating output electrical signals in response thereto. These output electrical signals are used by the remainder of ultrasound imaging system (not shown) to generate a visual display of information. Preferably head 104 is adjustable with several degrees of freedom to allow for different angles of view. Ring 102 further having a cannula receiving slot 106 therein at its top side 107. Cannula 108 is shown disposed in slot 106. Cannula 108 being preferably a stainless steel tubular member having an instrument receiving hole 110 therein. Slot 106 is formed by a right cannula retaining ridge 112 and a left cannula retaining ridge 114 which are at each protuberances disposed on the ring 102 at its top side 107. Slot 106 preferably having several concentric ridges or protuberances of decreasing separation therein (not shown) for receiving cannulas of decreasing size. Preferably, the concentric ridges are sufficiently resilient to retain a cannula therebetween. Probe 100 having a longitudinal shaft 116 extending from ring 102 to connector cable 118. Shaft 116 preferably having a cannula receiving groove 120 therein and being constructed of similar material as the ring 102.

In a typical operation, the probe 100 is used as follows: the physician inserts his finger in the palm end opening 101 of ring 102 so that the physician's finger tip extends through the ring 102 and beyond the tip end opening 103. The ring 102 can then be rotated around the finger to a comfortable position. The transducer head 104 is pivoted or adjusted to a pre-determined position so that a pre-determined relative angle exists between the head 104 and longitudinal shaft 116. This adjustment provides for varying viewing angles and therefore varying possible images. Typically a sterile Latex sheath or rubber glove or the like (not shown) is then pulled over the finger and probe 100 combination. The cannula 108, of the appropriate size is snapped into the slot between the appropriate concentric ridges with the sheath being disposed between the cannula 108 and the slot 106. A needle or other medical instrument is then partially inserted through hole 110 into the cannula. At this time the finger, probe 100, sheath, cannula 108, and the needle combination can be inserted into the rectum. Alternately, the needle may be inserted into hole 110 of cannula 106 after the finger, probe 100, sheath, and cannula 106 combination are inserted in the rectum. Various other procedures may also be used. During the time when the probe 100 is inserted into the rectum, it is capable of generating, with the aid of the ultrasound imaging system, (not shown), and image inside the rectum. Moreover, the physician is free to palpate the imaged area with his finger tip while also being free to manipulate the needle or medical instrument with his other fingers or hand. The ability to both view the imaged area and to concurrently touch and sense that area is a distinct advantage of the present invention. After the examination is complete, the sheath and cannula may be disposed and the probe reused.

It is thought that the probe of the present invention and many of its attendant advantages will be understood from the foregoing description and it will be apparent that various changes may be made to the form construction and arrangement of the parts thereof. Without departing from the spirit and scope of the invention or sacrificing all of its material advantages, the form hereinbefore described being a preferred or exemplary embodiment thereof. It is the intention of the appended claims to cover all such changes.

We claim:

1. An ultrasound transducer probe for cooperation with the finger of a medical professional and further cooperating the an ultrasound imaging system, of a type that produces a visual display when coupled with an ultrasound transducer probe, the ultrasound transducer probe comprising in cooperative combination:

an annular member having a top side, a bottom side, an interior side, and exterior side, a palm end opening, and a finger tip end opening;

said annular member further having an ultrasound transducer head coupled to said top side for generating a transmitted ultrasound signal in response to an input electrical signal for producing an output electrical signal in response to a received reflected ultrasound signal;

an elongated cylinder coupled with said annular member having an interior surface, an exterior surface, an annular member end, a connecting cable end and a longitudinal dimension extending from said annular member end to said connecting cable end;

a connecting cable coupled with said ultrasound transducer head for carrying said input electrical signal and said output electrical signal;

said cable being disposed with said cylinder;

a plurality of cannula receiving ridges coupled to said top side of said annular member;

a plurality of cannula retaining protuberances coupled to said exterior surface of said cylinder;

said transducer head being pivotably attached to said annular member, so that said transducer head is maintainable at various angles with respect to said longitudinal dimension of said cylinder.

2. A method for performing rectal examinations of the prostate gland comprising the steps of:

inserting the physician's finger into an annular member having an ultrasound transducer thereon which is coupled with an ultrasound imaging system;

covering the annular member and finger with a sterile sheath;

attaching a cannula to the annular member with the sheath disposed therebetween;

inserting the annular member, finger, sheath, and cannula into the patient's rectum;

guiding the transducer head into proximity with the prostate gland;

inserting a medical instrument into the cannula and observing the instrument with the imaging system.

3. A medical device comprising:

a ring of the type having an inside surface for receiving and securely engaging a human finger therein, and further having an outside surface; the ring having a transducer coupled to the outside surface, so that movement of the ring by a human finger engaged therein results in a movement of the transducer; a cable coupled with the transducer; and, means for coupling a biopsy needle with the ring.

4. A medical device of claim 3 wherein the means for coupling comprises means for receiving a guide tube.

5. A medical device of claim 4 wherein the means for receiving a guide tube provides for detachably coupling a guide tube with the ring.

6. A medical device of claim 5 wherein the means for receiving comprises at least two ridges disposed on the ring.

7. A medical device of claim 6 further comprising a cylinder coupled with the ring, and surrounding the cable.

8. A medical device of claim 7 further comprising second means for receiving a guide tube, disposed on the cylinder.

9. A medical device of claim 7 where the transducer is adjustably coupled to the ring.

10. A medical device of claim 7 where the transducer is pivotably adjustably coupled to the ring.

11. A medical device of claim 4 wherein the means for receiving provides for a permanently attached guide tube.

12. A medical device of claim 11 where the transducer is adjustably coupled to the ring.

13. A medical device of claim 12 where the transducer is pivotably adjustably coupled to the ring.

14. A medical device of claim 3 where the transducer is adjustably coupled to the ring.

15. A medical device of claim 3 where the transducer is pivotably adjustably coupled to the ring.

* * * * *